US 6,535,756 B1

(12) United States Patent
Simon et al.

(10) Patent No.: US 6,535,756 B1
(45) Date of Patent: Mar. 18, 2003

(54) TRAJECTORY STORAGE APPARATUS AND METHOD FOR SURGICAL NAVIGATION SYSTEM

(75) Inventors: David Anthnoy Simon, Boulder, CO (US); Kevin T. Foley; Thomas Andrew Carls, both of Memphis, TN (US); Anthony J. Melkent, Germantown, TN (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 0 days.

(21) Appl. No.: 09/545,092

(22) Filed: Apr. 7, 2000

(51) Int. Cl.$^7$ .................................................. A61B 5/05
(52) U.S. Cl. ........................ 600/424; 606/130; 378/205
(58) Field of Search ................................ 600/424, 411, 600/427; 606/130; 378/205

(56) References Cited

U.S. PATENT DOCUMENTS

| | | | |
|---|---|---|---|
| 3,702,935 A | 11/1972 | Carey et al. ................... 250/58 |
| 4,054,881 A | 10/1977 | Rab ......................... 343/112 R |
| 4,259,725 A | 3/1981 | Andrews et al. ............. 364/521 |
| 4,314,251 A | 2/1982 | Raab ........................ 343/112 R |
| 4,485,815 A | 12/1984 | Amplatz et al. ........ 128/329 R |
| 4,613,866 A | 9/1986 | Blood ......................... 343/448 |
| 4,618,978 A | 10/1986 | Cosman ....................... 378/164 |
| 4,722,056 A | 1/1988 | Roberts et al. .............. 364/413 |
| 4,742,815 A | 5/1988 | Ninan et al. |
| 4,750,487 A | 6/1988 | Zanetti ........................ 128/303 |
| 4,791,934 A | 12/1988 | Brunnett ...................... 128/653 |
| 4,896,673 A | 1/1990 | Rose et al. ............. 128/660.03 |
| 5,042,486 A | 8/1991 | Pfeiler et al. ............ 128/653 R |
| 5,078,140 A | 1/1992 | Kwoh ..................... 128/653.1 |
| 5,086,401 A | 2/1992 | Glassman et al. ............. 395/94 |
| 5,097,839 A | 3/1992 | Allen ...................... 128/653.1 |
| 5,119,817 A | 6/1992 | Allen ...................... 128/653.1 |

(List continued on next page.)

FOREIGN PATENT DOCUMENTS

| | | | |
|---|---|---|---|
| DE | 3717871 C2 | 12/1988 | ........... A61B/19/00 |
| DE | 3717871 A1 | 12/1988 | ........... A61B/19/00 |
| DE | 3838011 A1 | 7/1989 | ........... A61B/19/00 |
| DE | 4225112 C1 | 12/1993 | ........... A61B/19/00 |

(List continued on next page.)

OTHER PUBLICATIONS

Adams, L., et al., *Computer–Assisted Surgery*, IEEE Computer Graphics & Applications, pp. 43–51 (May 1990).

Adams, L., et al., *Aide au Reperage Tridimensionnel pour la Chirurgie de la Base du Crane*, Innov. Tech. Biol. Med., vol. 13, No. 4, pp. 409–424 (1992).

Benzel, E., et al., *Magnetic Source Imaging: A Review of the Magnes System of Biomagnetic Technologies Incorporated*, Neurosurgery, vol. 33, No. 2, (Aug. 1993).

(List continued on next page.)

Primary Examiner—Marvin M. Lateef
Assistant Examiner—Jeoyuh Lin
(74) Attorney, Agent, or Firm—Harness, Dickey & Pierce, P.L.C.

(57) ABSTRACT

Apparatus and methods are disclosed for use within an image-guided surgical navigation system for the storage and measurement of trajectories for surgical instruments. An icon representing the real-time trajectory of a tracked instrument is overlaid on one or more pre-acquired images of the patient. At the surgeon's command, the navigation system can store multiple trajectories of the instrument and create a static icon representing each saved trajectory for display. The surgeon may also measure a planar angle between any two trajectories. The angle is computed in the plane of the image, and therefore will be computed separately for each image displayed. Furthermore, the surgeon has the option of computing and displaying the three-dimensional distance between two points defined by any two trajectories.

46 Claims, 5 Drawing Sheets

U.S. PATENT DOCUMENTS

| | | | |
|---|---|---|---|
| 5,142,930 A | 9/1992 | Allen et al. | 74/469 |
| 5,160,337 A | 11/1992 | Cosman | 606/130 |
| 5,161,536 A | 11/1992 | Vilkomerson et al. | 128/660.07 |
| 5,178,164 A | 1/1993 | Allen | 128/898 |
| 5,186,174 A | 2/1993 | Schlondorff et al. | 128/653.1 |
| 5,198,877 A | 3/1993 | Schulz | 356/375 |
| 5,211,164 A | 5/1993 | Allen | 128/653.1 |
| 5,211,165 A | 5/1993 | Dumoulin et al. | 128/653.1 |
| 5,221,283 A * | 6/1993 | Chang | |
| 5,222,499 A | 6/1993 | Allen et al. | 128/653.1 |
| 5,230,338 A | 7/1993 | Allen et al. | 128/653 |
| 5,230,623 A | 7/1993 | Guthrie et al. | 433/72 |
| 5,249,581 A | 10/1993 | Horbal et al. | 128/664 |
| 5,251,127 A | 10/1993 | Raab | 364/413.13 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,261,404 A | 11/1993 | Mick et al. | 128/653.1 |
| 5,265,610 A | 11/1993 | Darrow et al. | 128/653.1 |
| 5,271,400 A | 12/1993 | Dumoulin et al. | 128/653.2 |
| 5,274,551 A | 12/1993 | Corby, Jr. | 364/413.13 |
| 5,279,309 A | 1/1994 | Taylor et al. | 128/782 |
| 5,295,483 A | 3/1994 | Nowacki et al. | 128/660 |
| 5,299,288 A | 3/1994 | Glassman et al. | 395/80 |
| 5,305,203 A | 4/1994 | Raab | 364/413.13 |
| 5,309,913 A | 5/1994 | Kormos et al. | 128/653.1 |
| 5,318,025 A | 6/1994 | Dumoulin et al. | 128/653.2 |
| 5,345,938 A | 9/1994 | Nishiki et al. | 128/660.04 |
| 5,353,795 A | 10/1994 | Souza et al. | 128/653.2 |
| 5,359,417 A | 10/1994 | Muller et al. | 356/375 |
| 5,369,678 A | 11/1994 | Chiu et al. | 378/62 |
| 5,377,678 A | 1/1995 | Dumoulin et al. | 128/653.1 |
| 5,383,454 A | 1/1995 | Bucholz | 128/653.1 |
| 5,389,101 A | 2/1995 | Heilbrun et al. | 606/130 |
| 5,391,199 A | 2/1995 | Ben-Haim | 607/122 |
| 5,397,329 A | 3/1995 | Allen | 606/73 |
| 5,398,684 A | 3/1995 | Hardy | 128/653.1 |
| 5,402,801 A | 4/1995 | Taylor | |
| 5,408,409 A | 4/1995 | Glassman et al. | 364/413.13 |
| 5,419,325 A | 5/1995 | Dumoulin et al. | 128/653.2 |
| 5,437,277 A | 8/1995 | Dumoulin et al. | 128/653.1 |
| 5,443,066 A | 8/1995 | Dumoulin et al. | 128/653.1 |
| 5,443,489 A | 8/1995 | Ben-Haim | 607/115 |
| 5,445,144 A | 8/1995 | Wodicka et al. | 128/207.14 |
| 5,445,150 A | 8/1995 | Dumoulin et al. | 128/653.1 |
| 5,480,422 A | 1/1996 | Ben-Haim | 607/122 |
| 5,483,961 A | 1/1996 | Kelly et al. | |
| 5,494,034 A | 2/1996 | Schlöndorff et al. | 128/653.1 |
| 5,515,160 A | 5/1996 | Schulz et al. | 356/241 |
| 5,517,990 A | 5/1996 | Kalfas et al. | 128/653.1 |
| 5,546,951 A | 8/1996 | Ben-Haim | 128/702 |
| 5,551,429 A | 9/1996 | Fitzpatrick et al. | 128/653.1 |
| 5,558,091 A | 9/1996 | Acker et al. | 128/653.1 |
| 5,568,809 A | 10/1996 | Ben-haim | 128/656 |
| 5,572,999 A | 11/1996 | Funda et al. | 128/653.1 |
| 5,575,798 A | 11/1996 | Koutrouvelis | 606/130 |
| 5,590,215 A | 12/1996 | Allen | 382/128 |
| 5,603,318 A | 2/1997 | Heilbrun et al. | 128/630 |
| 5,617,857 A | 4/1997 | Chader et al. | 128/653.1 |
| 5,622,170 A | 4/1997 | Schulz | 128/653.1 |
| 5,630,431 A | 5/1997 | Taylor | 128/897 |
| 5,638,819 A | 6/1997 | Manwaring et al. | 128/653.1 |
| 5,647,361 A | 7/1997 | Damadian | 128/683.2 |
| 5,662,111 A | 9/1997 | Cosman | 128/653.1 |
| 5,676,673 A | 10/1997 | Ferre et al. | 606/130 |
| 5,682,890 A | 11/1997 | Kormos et al. | 128/653.2 |
| 5,694,945 A | 12/1997 | Ben-Haim | 128/736 |
| 5,695,500 A | 12/1997 | Taylor et al. | 606/130 |
| 5,695,501 A | 12/1997 | Carol et al. | 606/130 |
| 5,711,299 A * | 1/1998 | Manwaring et al. | |
| 5,713,946 A | 2/1998 | Ben-Haim | 607/122 |
| 5,715,822 A | 2/1998 | Watkins et al. | 128/653.5 |
| 5,715,836 A | 2/1998 | Kliegis et al. | |
| 5,718,241 A | 2/1998 | Ben-Haim et al. | 128/702 |
| 5,727,553 A | 3/1998 | Saad | 128/653.1 |
| 5,729,129 A | 3/1998 | Acker | 324/207.12 |
| 5,730,129 A | 3/1998 | Darrow et al. | 128/653.1 |
| 5,732,703 A | 3/1998 | Kalfas et al. | 128/653.1 |
| 5,740,802 A | 4/1998 | Nafis et al. | 128/653.1 |
| 5,748,767 A | 5/1998 | Raab | 382/128 |
| 5,749,362 A | 5/1998 | Funda et al. | 128/653.1 |
| 5,752,513 A | 5/1998 | Acker et al. | 128/653.1 |
| 5,752,962 A * | 5/1998 | D'rso | |
| 5,755,725 A | 5/1998 | Druais | 606/130 |
| 5,769,861 A | 6/1998 | Vilsmeier | 606/130 |
| 5,772,594 A | 6/1998 | Barrick | 600/407 |
| 5,776,064 A | 7/1998 | Kalfas et al. | 600/414 |
| 5,787,886 A | 8/1998 | Kelly et al. | 128/653.1 |
| 5,795,294 A | 8/1998 | Luber et al. | 600/407 |
| 5,797,849 A | 8/1998 | Vesely et al. | 600/461 |
| 5,799,055 A | 8/1998 | Peshkin et al. | 378/42 |
| 5,800,352 A | 9/1998 | Ferre et al. | 600/407 |
| 5,810,728 A | 9/1998 | Kuhn | 600/410 |
| 5,823,958 A | 10/1998 | Truppe | 600/426 |
| 5,829,444 A | 11/1998 | Ferre et al. | 128/897 |
| 5,833,627 A | 11/1998 | Shmulewitz et al. | 600/562 |
| 5,834,759 A | 11/1998 | Glossop | 250/203.1 |
| 5,836,954 A | 11/1998 | Heilbrun et al. | 606/130 |
| 5,840,025 A | 11/1998 | Ben-Haim | 600/424 |
| 5,843,076 A | 12/1998 | Webster, Jr. et al. | 606/41 D |
| 5,851,183 A | 12/1998 | Bucholz | 600/425 |
| 5,868,675 A | 2/1999 | Henrion et al. | 600/424 |
| 5,871,445 A | 2/1999 | Bucholz | 600/407 |
| 5,873,822 A | 2/1999 | Ferre et al. | 600/407 |
| 5,882,304 A | 3/1999 | Ehnholm et al. | 600/411 |
| 5,891,034 A | 4/1999 | Bucholz | 600/426 |
| 5,907,395 A | 5/1999 | Schulz et al. | 356/139.03 |
| 5,913,820 A | 6/1999 | Bladen et al. | 600/407 |
| 5,920,395 A | 7/1999 | Schulz | 356/375 |
| 5,921,992 A | 7/1999 | Costales et al. | 606/130 |
| 5,947,981 A | 9/1999 | Cosman | 606/130 |
| 5,967,982 A | 10/1999 | Barnett | 600/429 |
| 5,971,997 A | 10/1999 | Guthrie et al. | 606/130 |
| 5,980,535 A | 11/1999 | Barnett et al. | 606/130 |
| 5,987,349 A | 11/1999 | Schulz | 600/427 |
| 5,987,960 A | 11/1999 | Messner et al. | 73/1.79 |
| 5,999,837 A | 12/1999 | Messner et al. | 600/407 |
| 6,006,126 A | 12/1999 | Cosman | 600/426 |
| 6,006,127 A | 12/1999 | Van Der Brug et al. | 600/427 |
| 6,013,087 A | 1/2000 | Adams et al. | 606/130 |
| 6,016,439 A | 1/2000 | Acker | 600/411 |
| 6,019,725 A | 2/2000 | Vesely et al. | 600/447 |
| 6,021,342 A | 2/2000 | Brabrand | 600/427 |
| 6,149,592 A * | 11/2000 | Yanof et al. | |
| 6,246,898 B1 * | 6/2001 | Vessely et al. | |

FOREIGN PATENT DOCUMENTS

| | | | | |
|---|---|---|---|---|
| DE | 4233978 | | 4/1994 | A61B/19/00 |
| DE | 19715202 A1 | | 10/1998 | A61B/19/00 |
| DE | 19751761 A1 | | 10/1998 | A61B/19/00 |
| DE | 19747427 A1 | | 5/1999 | A61B/19/00 |
| EP | 0 326 768 A2 | | 8/1989 | A61B/19/00 |
| EP | 0 359 773 B1 | | 3/1990 | A61B/6/02 |
| EP | 0 419 729 A1 | | 4/1991 | A61B/5/06 |
| EP | 0 427 358 A1 | | 5/1991 | A61B/6/00 |
| EP | 0 456 103 A2 | | 11/1991 | A61B/19/00 |
| EP | 0 469 966 A1 | | 2/1992 | A61B/19/00 |
| EP | 0 501 993 B1 | | 9/1992 | G06T/17/00 |
| EP | 0 655 138 B1 | | 5/1995 | G01S/3/14 |
| EP | 0 894 473 A2 | | 2/1999 | A61B/8/12 |
| EP | 0 908 146 A2 | | 4/1999 | A61B/17/17 |

| | | | | |
|---|---|---|---|---|
| EP | 0 930 046 A2 | 7/1999 | ............ | A61B/6/00 |
| WO | WO 88/09151 | 12/1988 | ............ | A61B/19/00 |
| WO | WO 91/03982 | 4/1991 | ............ | A61B/17/16 |
| WO | WO 91/07726 | 5/1991 | ............ | G06F/15/72 |
| WO | WO 92/06645 | 4/1992 | ............ | A61B/19/00 |
| WO | WO 94/04938 | 3/1994 | ............ | G01S/3/14 |
| WO | WO 94/23647 | 10/1994 | ............ | A61B/5/05 |
| WO | WO 94/24933 | 11/1994 | ............ | A61B/5/05 |
| WO | WO 95/07055 | 3/1995 | ............ | A61B/19/00 |
| WO | WO 96/11624 | 4/1996 | | |
| WO | WO 96/32059 | 9/1996 | ............ | A61B/5/055 |
| WO | WO97/03609 | 2/1997 | ............ | A61B/17/17 |
| WO | WO 97/31581 | 9/1997 | ............ | A61B/19/00 |
| WO | WO 97/36192 | 10/1997 | ............ | G01V/15/00 |
| WO | WO 97/40764 | 11/1997 | ............ | A61B/19/00 |
| WO | WO 99/15097 | 4/1999 | ............ | A61B/19/00 |
| WO | WO 99/21498 | 5/1999 | ............ | A61B/17/56 |
| WO | WO 99/23956 | * 5/1999 | | |
| WO | WO 99/26549 | 6/1999 | ............ | A61B/19/00 |
| WO | WO 99/27839 | 6/1999 | | |
| WO | WO 99/29253 | 6/1999 | ............ | A61B/19/00 |
| WO | WO 99/33406 | 7/1999 | ............ | A61B/19/00 |
| WO | WO 99/38449 | 8/1999 | ............ | A61B/19/00 |
| WO | WO 99/52094 | 10/1999 | ............ | G09G/3/02 |

OTHER PUBLICATIONS

Bouazza–Marouf, K., et al., *Robotic assisted internal fixation of femoral fractures*, Journal of Engineering in Medicine, Proc. Instn. Mech. Engrs., vol. 209, pp. 51–58 (1995).

Brunie, L., et al., *Pre– and intra–irradiation multimodal image registration: principles and first experiments*, Radiotherapy and Oncology 29, pp. 244–252 (1993).

Bucholz, R.D., et al., *Variables affecting the accuracy of stereotactic localization using computerized tomography*, J. Neurosurg., vol. 79, pp. 667–673 (1993).

Bucholz, R.D., et al., *A Comparison of Sonic Digitizers Versus Light Emitting Diode–Based Localization*, Interactive Image–guided Neurosurgery, Chapter 16, pp. 179–200 (1993).

Bucholz, R.D., et al., *Intraoperative localization using a three dimensional optical digitizer*, SPIE–The Intl. Soc. for Opt. Eng., vol. 1894, pp. 312–322 (Jan. 17–19, 1993).

Bucholz, R.D., et al., *Image–guided surgical techniques for infections and trauma of the central nervous system*, Neurosurg. Clinics of N.A., vol. 7, No. 2, pp. 187–200 (1996).

Bucholz, R.D., et al., *The Correction of Stereotactic Inaccuracy Caused by Brain Shift Using an Intraoperative Ultrasound Device*, First Joint Conference, Computer Vision, Virtual Reality and Robotics in Medicine and Medical Robotics and Computer–Assisted Surgery, Grenoble, France, pp. 459–466 (Mar. 19–22, 1997).

Bucholz, R.D., et al., *Intraoperative Ultrasonic Brain Shift Monitor and Analysis*, Stealth Station Marketing brochure (undated).

Cinquin, P., et al., *Computer Assisted Medical Interventions*, IEEE, pp. 254–263 (May/Jun. 1995).

Clarysse, P., et al., *A Computer–Assisted System for 3–D Frameless Localization in Stereotaxic MRI*, IEEE Trans. on Med. Imaging, vol. 10, No. 4, pp. 523–529 (Dec. 1991).

Foley, K.T., et al., *Image–guided spine surgery utilizing frameless stereotaxy*, Comparison and analysis (stamped confidential, undated).

Foley, K.T., et al., *Image–guided Intraoperative Spinal Localization*, Intraoperative Neuroprotection Chapter 19, pp. 325–340 (1996).

Gallen, C.C., et al., *Intracranial Neurosurgery Guided by Functional Imaging*, Surg. Neurol., vol. 42, pp. 523–530 (1994).

Galloway, R.L., et al., *Interactive Image–Guided Neurosurgery*, IEEE Trans. on Biomed. Eng., vol. 89, No. 12, pp. 1226–1231 (1992).

Germano, Isabelle M., et al., *The NeuroStation System for Image–Guided, Frameless stereotaxy*, Neurosurg., vol. 37, No. 2, pp. 348–350 (Aug. 1995).

Gomez, C.R., et al., *Transcranial Doppler Ultrasound Following Closed Head Injury: Vasospasm or Vasoparalysis?*, Surg. Neurol., vol. 35, pp. 30–35 (1991).

Grimson, W.E.L., et al., *Virtual–reality technology is giving surgeons the equivalent of x–ray vision helping them to remove tumors. . .* , Sci. Amer., vol. 280, No. 6, pp. 62–69 (Jun. 1999).

Hamadeh, A., *X–ray data acquisition in OR—Test Specificatioins, Operating Room Test Report*, Laboratoire TIMC, France, pp. 1–9 (Jun. 5, 1995).

Hamadeh, A., et al., *Toward automatic registration between CT and X–ray images: cooperation between 3D/2D registration and 2D edge detection*, TIMC–IMAG, Faculté de Medecine de Grenoble, France, pp. 39–46 (1995)(Second Annual Intl. Symposium on Medical Robotics and Computer–Assisted Surgery, MRCAS '95, Nov. 4–7, 1995).

Hatch, J.F., *Reference–Display System for the Integration of CT Scanning and the Operating Microscope*, IEEE, vol. 8, pp. 252–254, Proceedings of the Eleventh Annual Northeast Bioengineering Conference (Worcester, Massachusetts) (Mar. 14–15, 1985).

Heilbrun, M.P., et al., *Stereotactic localization and Guidance Using a Machine Vision Technique*, Stereotact. Funct. Neurosurg., Proceed. of the Mtg. of the Amer. Soc. for Stereot. and Funct. Neurosurg. (Pittsburgh, PA) vol. 58, pp. 94–98 (1992).

Heilbrun, M.P., *Progressive Technology Applications*, Neurosurgery for the Third Millenium, Chapter 15, pp. 191–198 (1992) (J. Whitaker & Sons Ltd., Amer. Assoc. of Neurol. Surgeons, Oct. 1992).

Henderson, J.M., et al., *An Accurate and Ergonomic Method of Registration for Image–guided Neurosurgery*, Computerized Medical Imaging and Graphics, vol. 18, No. 4, pp. 273–277 (1994).

Hofstetter, R., et al., *Fluoroscopy Based Surgical Navigation–Concept and Clinical Applications*, Computer Assisted Radiology and Surgery, CAR '97, Proceed. of the 11$^{th}$ Intl. Symp. and Exh., Berlin, pp. 956–960 (Jun. 25–28, 1997).

Kato, A., et al., *A frameless, armless navigational system for computer–assisted neurosurgery*, J. Neurosurg., vol. 74, pp. 845–849 (May 1991).

Klimek, L., et al., *Long–Term Experience with Different Types of Localization Systems in Skull–Base Surgery*, Ear, Nose & Throat Surgery, Chapter 51, pp. 635–638 (undated).

Krybus, W., et al., *Navigation Support for Surgery by Means of Optical Position Detection*, Computer Assisted Radiology Proceed. of the Intl. Symp. CAR '91 Computed Assisted Radiology, pp. 362–366 (Jul. 3–6, 1991).

Lavallée, S., et al., *Computer Assisted Interventionist Imaging: The Instance of Stereotactic Brain Surgery*, MEDINFO 89, pp. 613–617 (1989).

Lavallée, S., et al., *Computer Assisted Medical Interventions*, NATO ASI Series, vol. F 60, 3D Imaging in Medic., pp. 301–312 (1990).

Lavallée, S., et al., *Computer Assisted Spine Surgery: a technique for accurate transpedicular screw fixation*, TIMC, Faculté de Medecine de Grenoble (pp. 315–322,), J. of Image Guided Surg., vol. 1, No. 1, pp. 65–73 (1995).

Leavitt, D.D., et al., *Dynamic Field Shaping to Optimize Stereotactic Radiosurgery*, I.J. Rad. Onc. Biol. Phys., vol. 21, pp. 1247–1255 (1991).

Merloz, P., et al., *Computer assisted Spine Surgery*, Clinical Orthop. and Related Research, No. 337, pp. 86–96 (1997).

Pelizzari, C.A., et al., *Accurate Three–Dimensional Registration of CT, PET, and/or MR Images of the Brain*, Journal of Computer Assisted Tomography, vol. 13, No. 1, pp. 20–26 (Jan./Feb. 1989).

Potamianos, P., et al., *Manipulator Assisted Renal Treatment*, Centre for Robotics, Imperial College of Science, Technology & Medicine, London, pp. 214–226 (undated).

Reinhardt, H.F., et al., *Mikrochirurgische Entfernung . . . (Microsurgical removal of Deep–Seated Vascular Malformations Using Sonar Stereometry)*, Ultraschall in Med. 12, pp. 80–83 (1991).

Reinhardt, Hans F., *Neuronavigation: A Ten–Year Review*, Neurosurgery, pp. 329–341 (undated).

Reinhardt, H.F., et al., *Sonic Stereometry in Microsurgical Procedures for Deep–Seated Brain Tumors and Vascular Malformations*, Neurosurgery, vol. 32, No. 1, pp. 51–57 (Jan. 1993).

Sautot, P.P., *Computer assisted introduction of screws into pedicles*, Thesis, pp. 1–163 (undated).

Simon, D.A., et al., *Accuracy Validation in Image–Guided Orthopaedic Surgery*, Second Annual Intl. Symp. on Med. Rob. and Com.–Assisted Surgery, MRCAS '95, pp. 185–192 (1995).

Smith, K.R., et al., *Multimodality Image Analysis and Display Methods for Improved Tumor Localization in Stereotactic Neurosurgery*, Annual Intl. Conf. of the IEEE Eng. in Med. and Biol. Soc., vol. 13, No. 1, p. 210 (1991).

Smith, K.R., et al., *Computer Methods for Improved Diagnostic Image Display Applied to Stereotactic Neurosurgery*, Automedical, vol. 14, pp. 371–386 (1991).

Smith, K.R., et al., *The Neurostation™—a highly, accurate, minimally invasive solution to frameless stereotactic neurosurgery*, Comput. Med. Imag. and Graph., vol. 18, No. 4, pp. 247–256 (1994).

Troccaz, J., et al., *Conformal external radiotherapy of prostatic carconoma: requirements and experimental results*, Radiotherapy & Oncology 29, pp. 176–183 (1993).

Yeates, A., et al., *Simplified and Accurate CT–guided needle biopsy of central nervous system lesions*, J. Neurosurg., vol. 37, pp. 390–393 (1982).

Zinreich, S.J., *OR role seen for 3–D imaging*, reprinted from Radiology Today (Feb. 1991) (2 pages).

*Stereotactic One, Affordable PC Based Graphics for Stereotactic Surgery*, Stereotactic Image Systems, Inc. (SLC, Utah) (marketing brochure, undated).

BrainLab marketing brochures for Vector Vision (undated).

*Pixsys 3–D Digitizing Accessories*, by Pixsys (marketing brochure, undated).

Translation (from a French document) by Brian Fish, *Part C—Methodology for Computer Assisted Introduction of a Screw into a Pedicle*, Feb. 12, 2001.

\* cited by examiner

TRAJECTORY STORAGE APPARATUS AND METHOD FOR SURGICAL NAVIGATION SYSTEM

BACKGROUND OF THE INVENTION

1. Field of Invention

The present invention is directed generally to image-guided medical procedures, and more particularly, to systems and methods for the storage and geometric measurement of instrument trajectories used in image-based surgical guided navigation systems.

2. Description of the Related Art

Image based surgical techniques have been used with success in aiding physicians for performing a wide variety of delicate surgical procedures. These procedures are typically used when the visualization of a surgical tool could be obscured by a patient's anatomy, or when the surgical tool is visible but the patient's anatomy may be difficult to visualize in three dimensions. Such procedures include, for example, spinal implant placement, the alignment of broken bone fragments, and the fixation of bone fractures. Prior art techniques to accurately position a surgical instrument have included the use of x-ray images to localize its position. Through the repeated acquisition of x-ray images during the procedure, real-time placement of the instrument relative to the patient's anatomy can be displayed. More recently, virtual fluoroscopically-based surgical navigation systems have been employed to track an instrument trajectory and superimpose its representation onto pre-acquired images without requiring x-rays to be repeatedly taken during the actual surgical procedure.

In many situations, a surgeon would like to create a static visual reference using the real-time and generally instantaneous instrument trajectory displayed by the surgical navigation system as the instrument progresses in the general direction of a selected, desired path. For example, some procedures require the serial placement of several implants which must be placed in a precise relative geometry. Currently, the surgeon must reacquire a new set of images after each implant is placed to properly determine the trajectory of the subsequent implant. This can be a time consuming process which increases the amount of radiation exposure to the patient and operating room personnel.

Other situations may require the surgeon to make accurate geometric measurements of a patient's anatomy. For example, some surgical procedures require the precise removal of a specific amount of bone taken in the shape of a wedge. In order to determine this amount, an angular measurement of the bone at the surgical site would assist in this procedure. Another example would be in allowing the surgeon to make distance measurement between bone implant sites to ensure proper implant placement. In light of the foregoing, there is a need for the ability to save surgical instrument trajectories and have the capability to perform measurements thereon.

SUMMARY OF THE INVENTION

The present invention is directed generally to image guided medical procedures, and, particularly, to medical procedures involving the tracking of surgical instruments. More specifically, the present invention is directed to a device and method for storing instrument trajectories.

To achieve these objects and other advantages and in accordance with the purposes of the invention, as embodied and broadly described herein, the invention is directed to an apparatus and method for the storage of trajectories and measurements which may be performed thereon for use in conjunction with image-guided surgical navigation systems.

In one aspect of the invention, an instrument trajectory is tracked in real-time by a surgical navigation system. An icon representing this real-time trajectory is overlaid on one or more pre-acquired images of the patient. At the surgeon's command, the navigation system can store the trajectory of the instrument and, if desired, create a static icon representing the saved trajectory for display on each pre-acquired image. The icon representing the stored trajectory is simultaneously displayed with the real-time trajectory's icon so the surgeon may visually compare them. The surgeon has the option of saving additional trajectories by reissuing the storage command.

In another aspect of the invention, the surgeon may measure angles between pairs of any two trajectories. The angles are computed in the plane of the image, and are, therefore, computed separately for each image displayed. One option is to compute one or more angles between the real-time trajectory and saved trajectories. These angles are preferably computed and displayed on each pre-acquired image. As the real-time trajectory changes, the displayed values are preferably updated in each image in real-time. Another option is to measure one or more angles between pairs of any two stored trajectories. As with the prior option, these angles could be computed and displayed separately for each image.

In yet another aspect of the invention, three dimensional distances between pairs of points defined by one or more sets of two trajectories can be computed and displayed. One option is to measure the distance between the real-time trajectory and one or more saved trajectories. These measurements would be computed in real-time and updated on the display as the real-time trajectory varies. Another option would be computing and displaying distances between pairs of points defined by one or more sets of two user-selected stored trajectories. For either of these two options, the defined points may be represented by the tip of each trajectory as computed by the system, or may be defined by a user-selected extension projected from the trajectory's tip.

Preferably, the invention can overcome the problems of the prior art by providing the surgeon with the visual reference and measurement information required for some surgical procedures.

Both the foregoing general description and the following detailed description are exemplary, and are intended to provide further explanation of the invention as claimed.

BRIEF DESCRIPTION OF THE DRAWINGS

The accompanying drawings, which are incorporated in and constitute a part of this specification, illustrate an embodiment of the invention and together with the description, serve to explain the principles of the invention.

DETAILED DESCRIPTION

Reference will now be made in detail to the present preferred embodiments of the invention, examples of which are illustrated in the accompanying drawings. Wherever possible, the same reference numbers will be used throughout the drawings to refer to the same or like parts.

Figure 1:
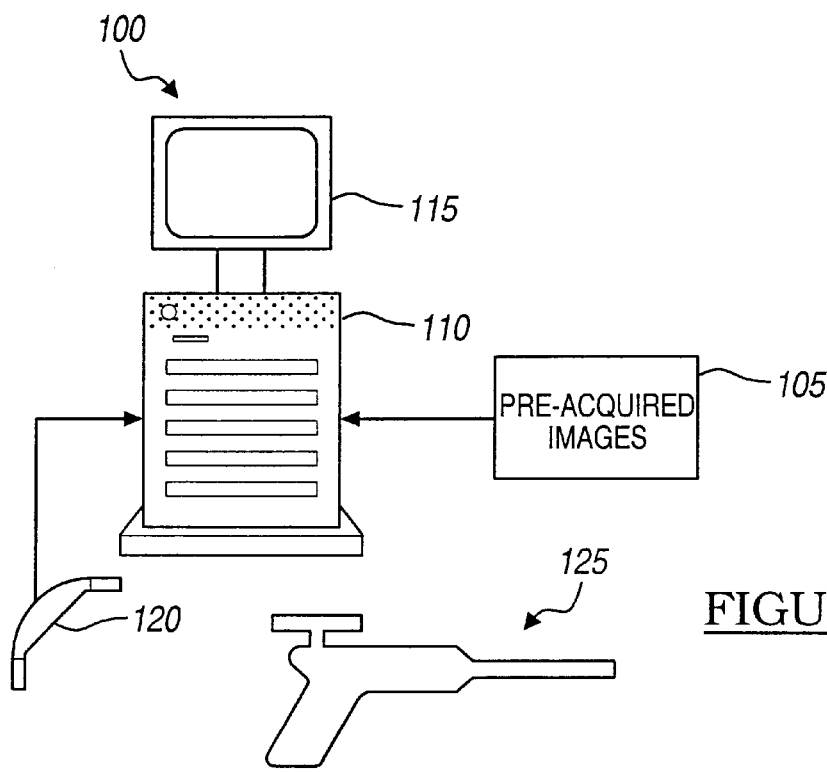
FIG. 1 is a simplified block diagram of an embodiment of a system for the storage and measurement of instrument trajectories in accordance with the present invention.

With reference to FIG. 1, there is shown schematically an apparatus in accordance with the present invention for the storage of instrument trajectories. Image-based surgical navigation system 100 enables a surgeon to generate and display on monitor 115 the trajectory of instrument 125, which is preferably a surgical instrument configured in any known manner. Data representing one or more pre-acquired images 105 is fed to navigation computer 110. Navigation computer 110 tracks the position of instrument 125 in real-time utilizing detector 120. Computer 110 then registers and displays the trajectory of instrument 125 with images 105 in real-time. An icon representing the trajectory of instrument 125 is superimposed on the pre-acquired images 105 and shown on monitor 115. At the surgeon's command, the real-time trajectory of instrument 125 can be stored in computer 110. This command also creates a new static icon representing the trajectory of the instrument on display 115 at the time the surgeon's command was issued. The surgeon has the option of issuing additional commands, each one storing an real-time trajectory and creating a new static icon for display by default. The surgeon can override this default and choose to not display any static icon. The surgeon also has the option to perform a number of geometric measurements using the real-time and stored instrument trajectories. While the present invention described in more detail below is exemplified by a fluoroscopic-based system, it is not limited to the described embodiment and could be practiced with many different types of navigation systems.

Figure 2:
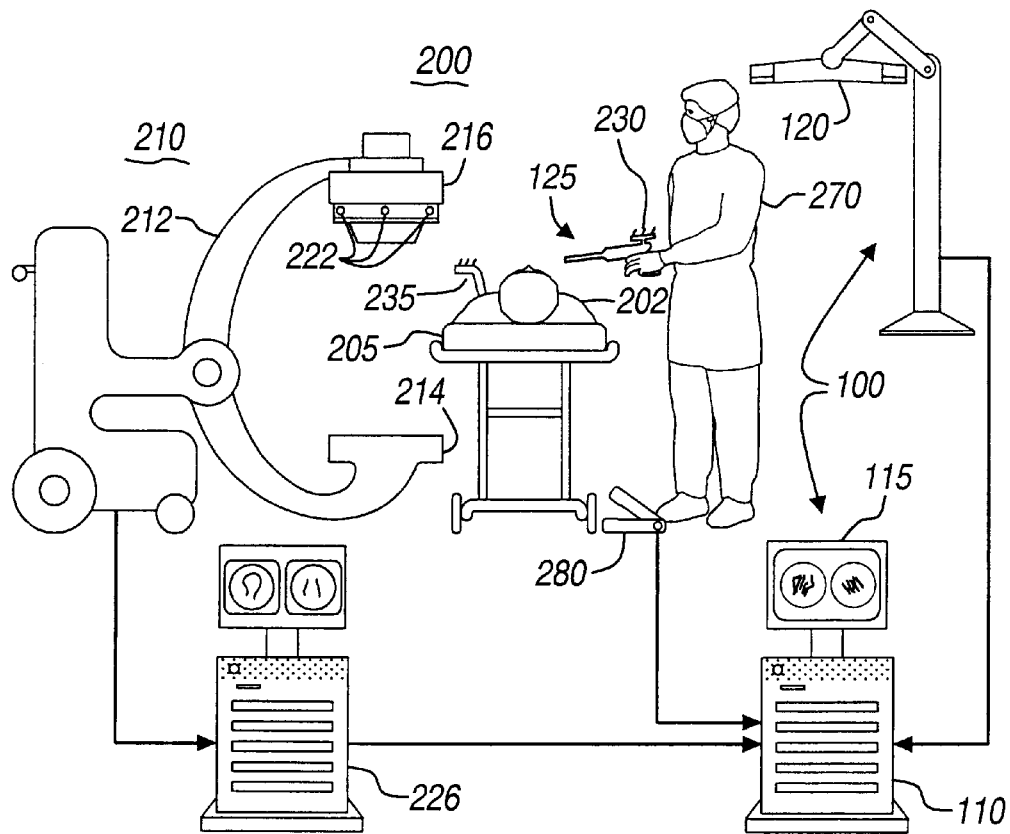
FIG. 2 is a simplified side view of an embodiment of a system for use in instrument trajectory storage and measurement in accordance with the present invention.

FIG. 2 illustrates fluoroscopic image-based surgical navigation system 200 according to the preferred embodiment of the present invention. System 200, described below in sufficient detail to allow an understanding and appreciation of the present invention, is explained in greater detail in U.S. patent application Ser. No. 09/274,972 of David A. Simon et al., entitled "Navigation Guidance via Computer Assisted Fluoroscopic Imaging," filed on Mar. 23, 1999, the entire disclosure of which is hereby incorporated by reference. However, it should be understood that the invention is not confined to use with this particular image guided surgical system.

Further referring to FIG. 2, an image-based surgical navigation system 200 for acquiring and displaying x-ray images appropriate for a given surgical procedure is shown. Pre-acquired images of patient 202 are collected when a patient, lying on platform 205, is placed within C-arm 212 of imaging device 210. The term "pre-acquired," as used herein, does not imply any specified time sequence. Preferably, however, the images are taken at some time prior to when surgical navigation is performed. Usually, images are taken from two substantially orthogonal directions, such as anterior-posterior (A-P) and lateral, of the anatomy of interest. Imaging system 210 further includes x-ray source 214 and x-ray receiving section 216 mounted on opposite sides of C-arm 212. Receiving section 216 includes target tracking markers 222. System 210 further includes C-arm control computer 226 which allows a physician to control the operation of imaging device 210. One implementation of imaging device 210 is the Model 9600 C-arm fluoroscope from OEC Medical Systems, Inc. of Salt Lake City, Utah, although tracking markers 222 are typically not included in the Model 9600 C-arm fluoroscope and may have to be added, however, the 9600 is otherwise structurally similar to imaging device 210. It is to be understood, however, that the invention is not confined to the use of this type of imaging device.

Fluoroscopic images taken by imaging system 210 are transmitted to computer 226 where they may be forwarded to surgical navigation computer 110. Computer 110 provides the ability to display the received images via monitor 115. Other devices, for example, such as heads up displays, may also be used to display the images.

Further referring to FIG. 2, image-based surgical navigation system 100 generally performs the real-time tracking of instrument 125, and, in the preferred embodiment, also tracks the position of receiver section 216 and reference frame 235. Detector 120 senses the presence of tracking markers on each object to be tracked. Detector 120 is coupled to computer 110 which is programmed with software modules that analyze the signals transmitted by detector 120 to determine the position of each object in detector space. The manner in which the detector localizes the object is known in the art, and is discussed, for example, in PCT Application No. PCT/US95/12894 (Publication No. WO 96/11624) to Bucholz, the entire disclosure of which is incorporated by reference. Any type of tracking system known in the art can be used, including, by way of example only, acoustic, optical, LED/reflectors, electromagnetic, and/or other similar devices.

In general, instrument 125 is tracked by surgical navigation system 100 using attached tracking markers 230 in order for its three-dimensional position to be determined in detector space. Computer 110 integrates this information with the pre-acquired images of patient 202 to produce a display which assists surgeon 270 when performing surgical procedures. An iconic representation of the trajectory of instrument 125 is simultaneously overlaid on the pre-acquired images of patient 202 and displayed on monitor 115. In this manner, surgeon 270 is able to see the trajectory of the instrument relative to the patient's anatomy in real-time.

Further referring to FIG. 2, the system according to the invention preferably has the ability to save the dynamic real-time trajectory of instrument 125. By issuing a command using foot-switch 280, for example, computer 110 receives a signal to store the real-time trajectory of the instrument in the memory of computer 110. This "storage command" also instructs computer 110 to generate a new static icon representing the saved trajectory of the instrument, essentially "freezing" the icon at the point when foot-switch 280 was closed. The static icon, along with the icon representing the real-time trajectory of the instrument, can be simultaneously superimposed over the pre-acquired image. If multiple images are being displayed, both static and real-time icons can be superimposed on all of the displayed images. Other means of issuing the storage command, such as, for example, through a graphical user interface, may also be used. The surgeon also has the option of storing multiple instrument trajectories. Each time a desired storage command is issued, the real-time trajectory of the instrument is stored in computer 110 and a new static icon representing the stored trajectory is displayed on the pre-acquired image, or if more than one image is being displayed, on all the pre-acquired images. These storage trajectory features are described in more detail below.

The system according to the invention preferably has the additional capability to measure angles between the real-time trajectory and one or more of the stored trajectories. These "dynamic angles" are measured in the image plane and are updated in real-time as the real-time trajectory varies. The computed values may then be displayed simultaneously with the pre-acquired image. If more than one pre-acquired image is being displayed, the angles for each image are preferably computed and displayed separately since they will be different for each image plane. Preferably, the system is configured to compute and display one or more angles between pairs of stored trajectories selected by surgeon 270. As with the dynamic angle measurements, the angles between the stored trajectories are computed in the image plane. They are preferably calculated and displayed separately for each displayed image. These angle calculation features will be described in more detail below.

Furthermore, the system preferably also has the ability to compute three-dimensional distances between pairs of points defined by the real-time trajectory and one or more stored trajectories selected by surgeon 270. These "dynamic distance" values are displayed with the image and vary as the instrument's trajectory changes. The system also preferably has the ability to measure distances between pairs of points defined by one or more pairs of stored trajectories and to display this information with the image. For either distance measuring option, the point pairs above may be defined by the tips of the instrument trajectories, or they may be defined by extending the tips by a user-specified amount. Each of these options will be discussed in more detail below. Unlike the angle calculation, the three-dimensional distance is not a planar measurement, as such it will not vary among different images. The distance parameters may be displayed separately for each image, or, as in the preferred embodiment, may only be displayed in one location.

Image-based surgical navigation system 100 utilized in the preferred embodiment of the present invention may be the same as that used in the FluoroNav™ system, which utilizes the StealthStation® Treatment Guidance Platform, both of which are available from Medtronic Sofamor Danek, Inc.

Figure 3:
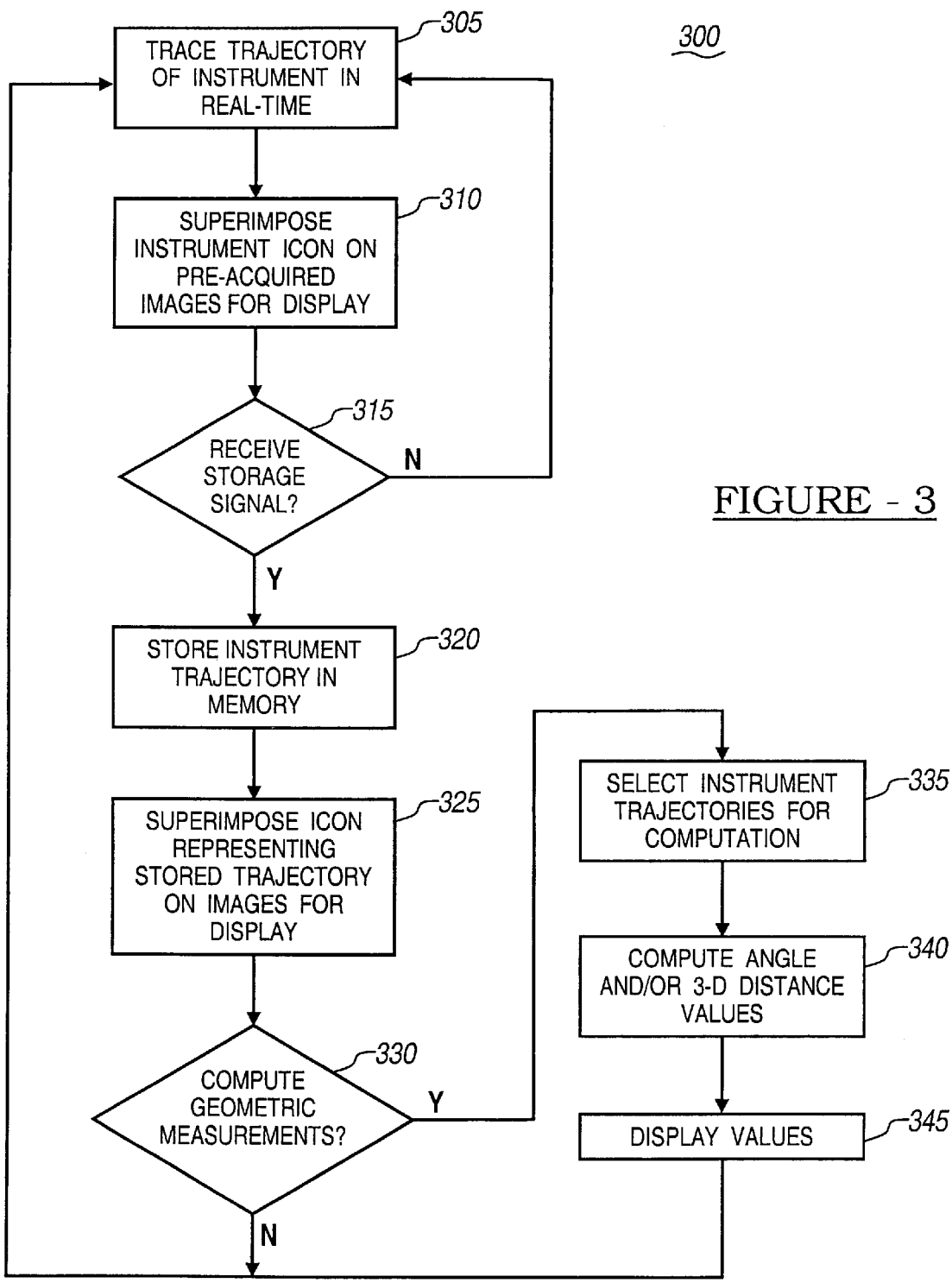
FIG. 3 is a block diagram of a process used to select, store, and compute geometric properties of trajectories in accordance with the present invention.

FIG. 3 shows flowchart 300 illustrating the preferred embodiment for storing instrument trajectories and computing geometric quantities. System 100 tracks instrument 125 by detecting tracking markers 230 with detector 120. Positions are computed in real-time in detector space by computer 110 and converted to frame space, which is a coordinate system associated with reference frame 235. The conversions used may be ones which are well known to those skilled in the art. The instrument trajectory is preferably tracked using two points, the tip and the hind, on instrument 125 which are obtained using known offsets from tracking markers 230 (step 305). The computation of the tip and hind positions is described in more detail below. An icon representing the real-time trajectory of instrument 125 may be superimposed on one or more pre-acquired images 105 (step 310). The real-time instrument tracking proceeds until the computer receives a storage command from the surgeon.

In the preferred embodiment, this command is given by a signal initiated by actuation of foot-switch 280. The surgeon may also use a graphical user interface, which is described in more detail below, running on computer 110 to issue a storage command (step 315). Upon receipt of the command, computer 110 stores the real-time trajectory of instrument 125 by placing the positions of the instrument's tip and hind into memory (step 320). Computer 110 then displays an icon representing the stored trajectory which may be superimposed, along with the real-time trajectory, on the pre-acquired image. If more than one pre-acquired image is being displayed, both the stored and real-time icons can be superimposed on all pre-acquired images (step 325).

After one or more trajectories are saved, surgeon 270 has the option of computing several geometric measurements through exercising the appropriate commands on the computer's 110 graphic interface (step 330). The surgeon will then typically select which trajectories to perform the measurements upon. Measurements may be performed between the real-time trajectory and one or more user-selected stored trajectories. Alternatively, a number of measurements may also be made between pairs of user-selected stored trajectories which are chosen through the user interface (step 335). Once the trajectory pairs are chosen, surgeon 270 can select to have the angles and/or a distance measurements performed (step 340). The distance and angle calculations are described below in more detail.

Finally, the values the surgeon chose to measure can be displayed on monitor 115 simultaneously with the pre-acquired image and trajectory icons. If the measurement being performed includes the real-time trajectory, each displayed value can be updated in real-time as the position of instrument 125 changes. If multiple pre-acquired images are being displayed, the angles can be displayed on each desired image. However, in the preferred embodiment, the distance values will typically be displayed in one location. (step 345).

Figure 4:
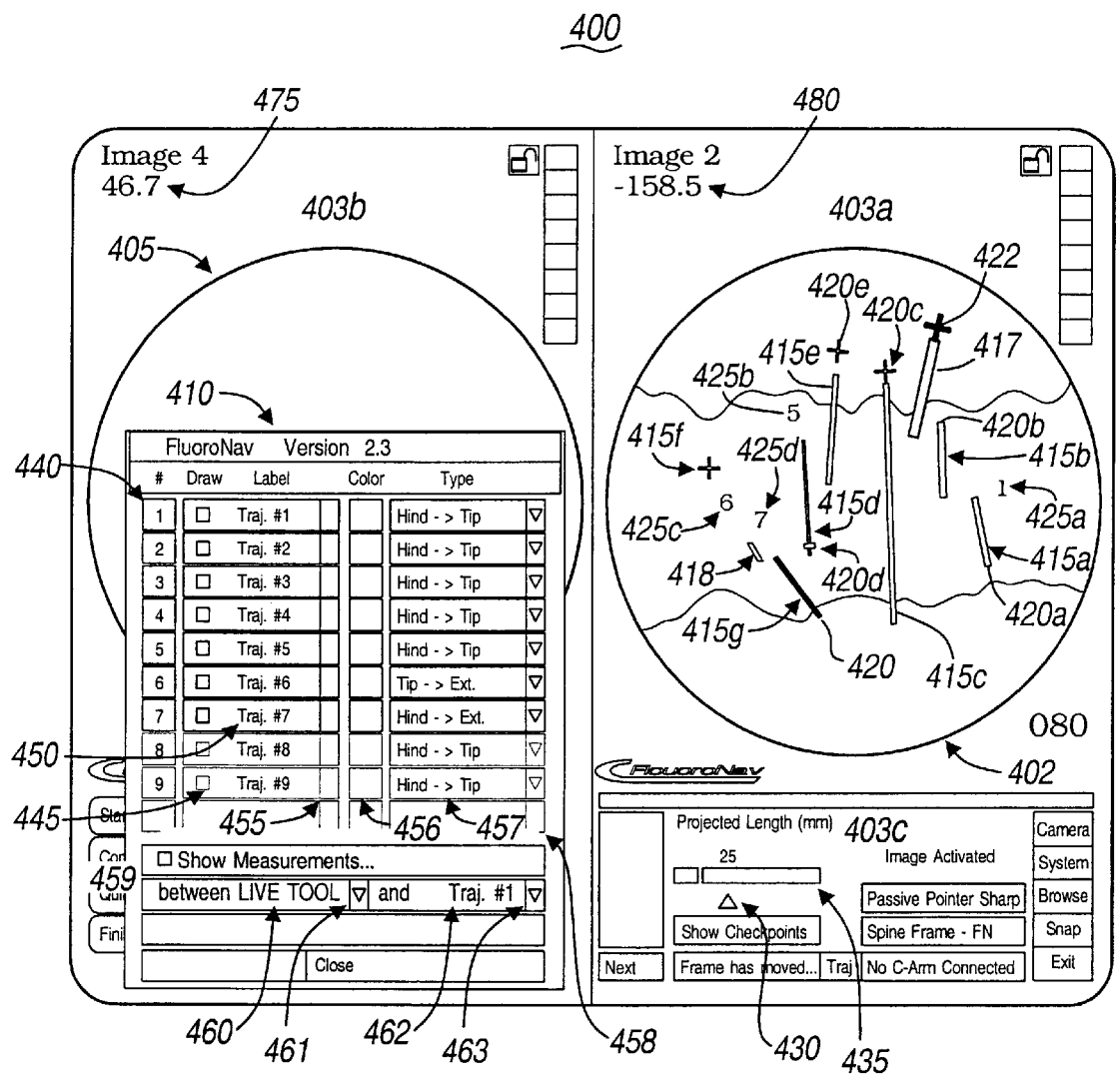
FIG. 4 is an exemplary diagram of a display in accordance with an embodiment of the invention showing several stored instrument trajectories and the real-time trajectory superimposed on two images of a patient's anatomy.

FIG. 4 shows an exemplary display which is consistent with the preferred embodiment of the invention. Display 400 preferably includes of three primary default windows, 403a–c. Two fluoroscopic images, 402 and 405, taken from different orientations of a patient, are shown in two windows, 403a–b, respectively. Control and status window 403c provides the surgeon with a set of software controls to vary the system parameters and control the modes and functionalities of the FluoroNav™ system. Note that image 405 is partially obscured by dialog box 410.

Further referring to FIG. 4, image 402 shows seven stored trajectories, 415a–g, and one real-time trajectory, 417. The hind points of each stored trajectory are denoted with cross symbols 420a–f. Note the cross symbol of trajectory 415f is not indicative of a hind point, but of an extension. Extensions will be described in more detail later. The hind point of real-time trajectory 417 is indicated by cross 422. Obviously, many other symbols other than a cross may be used to denote the hind point. Each trajectory, represented by a directional indicator such as a line, can be automatically assigned a different color and unique numerical label to easily identify it. Other types of directional indicators may also be used, and different shapes, styles, sizes, and textures can be employed to differentiate among the trajectories. Only labels 425a–d, associated with trajectories 415a, 415d, 415f, and 415g, respectively, are shown in window 403a. The surgeon has the option of not showing the label for any trajectory if desired. The surgeon also has the option of changing the default color or label text for any trajectory through the controls contained in dialog box 410. The functionality of dialog box 410 will be described in more detail below.

In certain situations, the surgeon may wish to know where the tip of the instrument would be if it were extended along a path direction indicated by its current trajectory. When software button 430 in window 403c is toggled on, computer 110 will calculate and display the icon based upon the previously set extension, as set by slider bar 435, and the current trajectory of the instrument. Toggling button 430 again will result in no extension being displayed. For example, if button 430 were previously activated and slider 435 is set to 45 mm, selecting button 430 will set the slider value to 0 mm. Activating it a second time will restore it to 45 mm. The estimated position of the tip can be calculated by computer 110 by projecting a fixed length beyond the instrument's tip in the direction of the line formed by each instrument's tip and hind. As shown in FIG. 4, an exemplary extension 418 is shown in a different line style from trajectory icon 415g. This difference could also be a change in color, type, and/or texture between extension 418 and current trajectory 415g. Computer 110 may vary the length of the extension as directed by the surgeon through manipulating control slider 435 using computer 110's mouse or keyboard. The extension feature is described in greater detail in U.S. patent application Ser. No. 09/274,972 which has been incorporated by reference. Although the look-ahead technique described above projects the graphical representation of the instrument into the image, there is no requirement that the instrument's graphical representation be in the space of the image for the extension to be projected into the image. In other words, for example, the surgeon may be holding instrument 125 above the patient and outside the space of the image, so that the representation of the instrument does not appear in the images. However, it may still be desirable to project ahead a fixed length into the image to facilitate planning of the procedure.

Further referring to FIG. 4, dialog box 410 allows the surgeon to control various aspects of how trajectories and labels are displayed. Whenever the surgeon initiates a command to store a trajectory, a row is automatically created in dialog box 410 and is identified by a number appearing in column 440. The surgeon has the option of removing a saved trajectory from display 403a by selecting the appropriate button in column 445. The color or texture of a button in column 445 can indicate the current icon display status.

Column 450 contains fields which indicate the text used in the labels for each stored trajectory. Computer 110 can select numerical values as defaults, which are illustrated in labels 425a–d, or the surgeon may select a custom label. This is accomplished by using computer 110's mouse to select the appropriate field of column 450 corresponding to the stored trajectory to be renamed. Once selected, the surgeon can use computer 110's keyboard to enter the desired text for the label. Furthermore, the label of each trajectory can be selectively displayed by activating the appropriate button in column 455 with the mouse. The color or texture of the button can be used to indicate the display status of the label for each stored trajectory. In this example, buttons corresponding to trajectories 1,5,6, and 7 are in the "on" state which results only in labels 425a–d being displayed in window 403a.

Selection of one of the buttons in column 456 causes the default color of the stored trajectory to be overridden by the user. Activation of the appropriate button displays a palette of colors from which one may choose to color the respective icon.

The surgeon also has the ability to select the mode of display for each icon. Selecting pull-down menu 458 allows the user to chose from one of three different display modes for each stored trajectory. The first mode, "Hind->Tip," creates an icon by drawing a line from the instruments hind position to the instruments tip position as shown in icons 415a–e. The second mode, "Tip->Ext.," creates an icon by drawing a line from the instrument's tip to the end of the extension. This mode is shown in icon 415f, which is displayed as a light colored cross to denote the extension. The third display mode, "Hind->Ext.," draws a line from the hind of the instrument to the tip of the extension. This mode is exemplified in icon 415g and extension 418. Column 457 indicates the display mode associated with each stored trajectory.

Further referring to FIG. 4, the surgeon has the option to have computer 110 compute and display measurements between selected trajectories. Button 459 commands computer 110 to display the measurements and allows the user to select which measurements to display. Pull-down menus 461, 463 allow the user to choose the trajectories which will be used to perform the measurements. Note that the real-time instrument may be used in conjunction with one or more pairs of any of the stored trajectories, or the measurements may be made against one or more pairs of any two saved trajectories. Text fields 460, 462 indicate which trajectories will be used in the measurement. The results of the measurement calculation will be displayed in windows 403a–b. In FIG. 4, the planar angle between real-time trajectory 417 and stored trajectory 415a is shown at 470 in window 403b and 480 in window 403a. The difference between values 470 and 480 is due to the different planar geometries associated with images 402 and 405.

Figure 5:
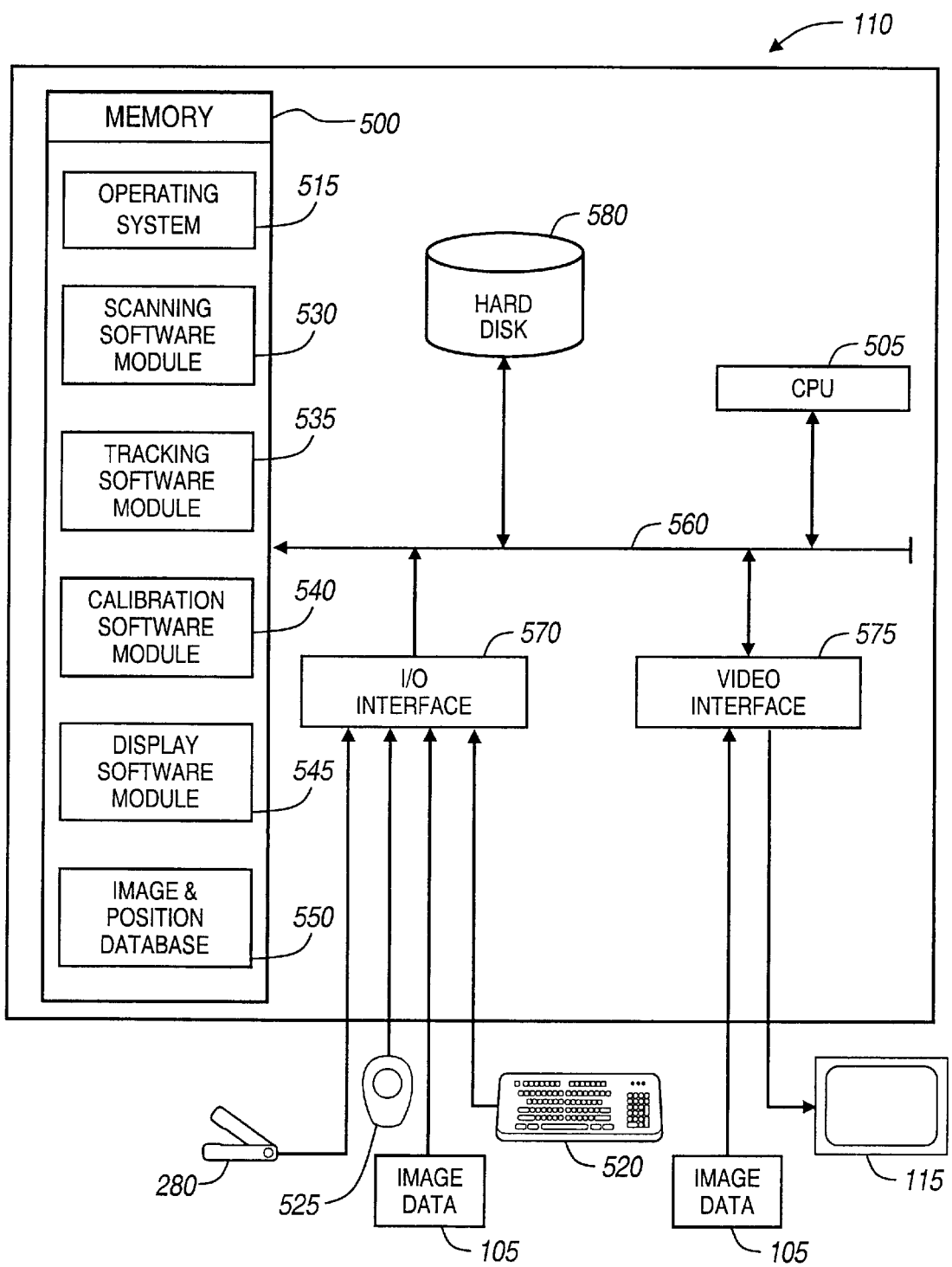
FIG. 5 is a simplified block diagram of an exemplary computer system used in the surgical navigation system in accordance with one embodiment of the invention.

Referring to FIG. 5, components and modules of a computer system 110 used to perform various processes of the present invention are described. Although a STEALTH STATION® image guided system manufactured by Medtronic Sofamor Danek has been identified, it will be appreciated that the present invention may be utilized with other types of computer systems. One aspect of the computer system 110 includes a graphical user interface system operating in conjunction with a display screen of a display monitor 115. The graphical user interface system is preferably implemented in conjunction with operating system 515 running computer 110 for displaying and managing the display objects of the system. The graphical user interface is implemented as part of the computer system 110 to receive input data and commands from a conventional keyboard 520 and mouse 525. Foot-switch 280 is also configured to enable the user to initiate the storage of instrument 125's real-time trajectory. For simplicity of the drawings and explanation, many components of a conventional computer system have not been illustrated such as address buffers, memory buffers, and other standard control circuits because these elements are well known in the art and a detailed description thereof is not necessary for understanding the present invention.

A computer program used to implement the various steps of the present invention is generally located in memory unit 500, and the processes of the present invention are carried out through the use of a central processing unit (CPU) 505. Those skilled in the art will appreciate that the memory unit 500 is representative of both read-only memory and random access memory. The memory unit also contains a database 550 that stores data, for example, image data and tables, including such information as stored instrument tip and hind positions, extension values, and geometric transform parameters, used in conjunction with the present invention. CPU 505, in combination with the computer software comprising operating system 515, scanning software module 530, tracking software module 535, calibration software module 540, and display software module 545, controls the operations and processes of computer system 110. The processes implemented by CPU 505 may be communicated as electrical signals along bus 560 to an I/O interface 570 and a video interface 575.

Scanning software module 530 performs the processes associated with creating a coordinate reference system and reference images for use in connection with the present invention and are known to those skilled in the art. Tracking software module 535 performs the processes necessary for tracking objects in an image guided system as described herein and are known to those skilled in the art. Calibration software module 640 computes the geometric transform which corrects for image distortions and registers the images to the anatomical reference frame 235, and thus the patient's anatomy.

Display software module 545 applies, and if desired, computes the offsets between the guide tracking markers 230 and the tip and hind of the instrument in order generate an icon representing the trajectory of the instrument for superposition over the images. For instruments with fixed lengths and angulations, these offsets can be measured once and stored in database 550. The user would then select from a list of instruments, the one being used in the procedure so the proper offsets are applied by display software module 545. For instruments with variable lengths and angulations, the offsets could be measured manually and entered via keyboard 520, or measured using the navigation system 100 in conjunction a tracked pointer or tracked registration jig (not shown). If a tracked pointer is used, the user will touch the tip and tail of the instrument while it is being tracked. The offsets are computed by display software module 545 and stored for later use. Similarly, if a tracked registration jig is used, the instrument is placed within the jig while it is being tracked. The jig will measure the extremities of the instrument and display software module 545 will again compute the offsets and store them for later use in database 550.

Pre-acquired image data 105 can be fed directly into computer 110 digitally through I/O interface 570, or may be supplied as video data through video interface 575. In addition, items shown as stored in memory can also be stored, at least partially, on hard disk 580 if memory resources are limited. Furthermore, while not explicitly shown, image data may also be supplied over a network, through a mass storage device such as a hard drive, optical disks, tape drives, or any other type of data transfer and storage devices which are known in the art.

Figure 6:
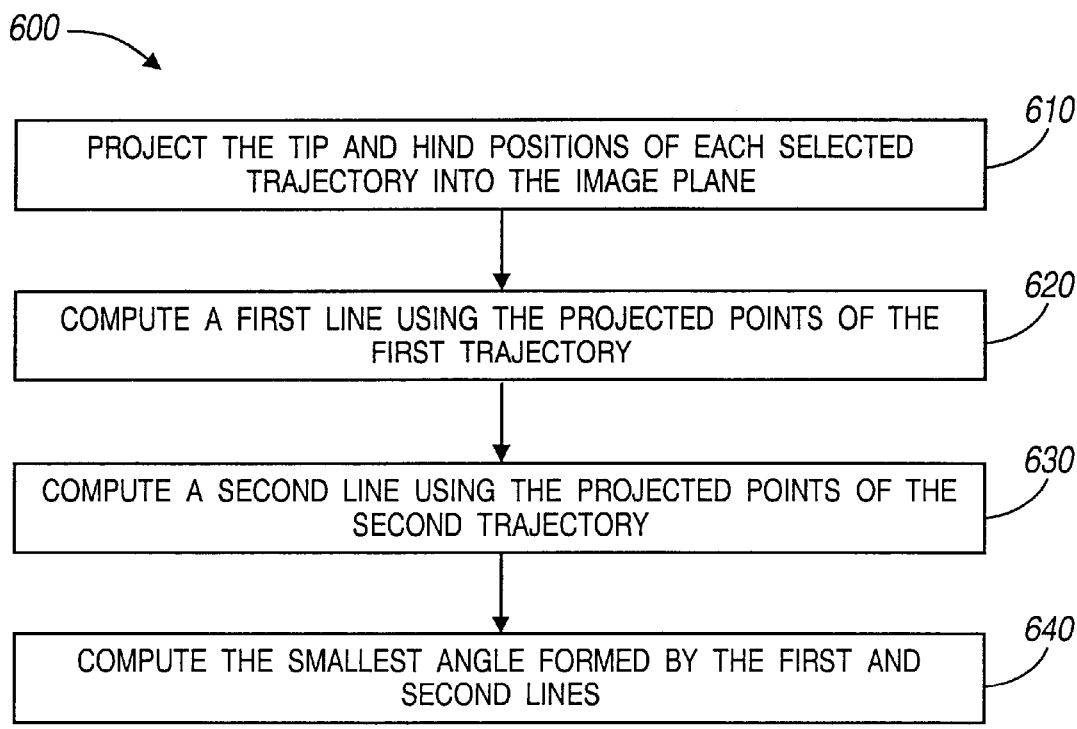
FIG. 6 is a block diagram of a process used compute the angle between two trajectories in accordance with the present invention.

FIG. 6 shows a block diagram illustrating a method for calculating a planar angle between two trajectories for the preferred embodiment. After surgeon 270 selects the trajectories using pull-down menus 461,463 as described above, the tip and the hind positions of each trajectory are projected into the image plane. Since x-ray receiving section 216 is tracked by navigation system 100 utilizing tracking markers 222, the coordinates of the image plane are well defined. Using the tip, hind, and image plane coordinates, the projection is performed using techniques well known to those skilled in the art (610). A first line segment is constructed by connecting the projected tip and hind points corresponding to the first trajectory computed above (step 620). In the same manner, a second line segment is constructed utilizing the projected points of the second trajectory (step 630). The angle corresponding to the intersections of the two aforementioned line segments can then be computed by techniques known to those skilled in the art (step 640).

Figure 7:
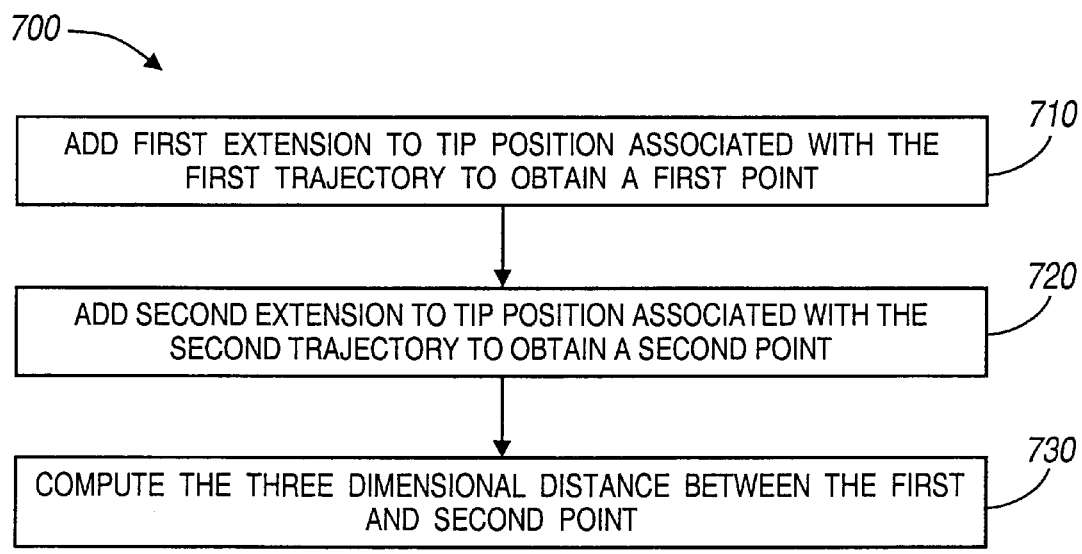
FIG. 7 is a is a block diagram of a process used compute the distance between the tips of two trajectories in accordance with the present invention.

FIG. 7 shows a block diagram illustrating a method of the preferred embodiment for calculating a distance between points in space as defined by two trajectories. After surgeon 270 selects two trajectories using pull-down menus 461, 463 in the manner described above, a first point is determined using the three-dimensional tip position of the first trajectory as computed by navigation system 100. If a "look-ahead" extension is associated with the first trajectory, it is added to the tip position (step 710). A second point associated with the second trajectory is computed in the same manner as described for step 710 (step 720). The distance may then be computed using the three-dimensional coordinates of the first and second points by a standard Euclidean distance formula which is well known in the art.

The foregoing description is presented for purposes of illustration and explanation. It is not intended to be exhaustive or to limit the invention to the precise form disclosed, and modifications of variations are possible in light of the above teachings or may be acquired from practice of the invention. The principles of the invention and its practical application enable one skilled in the art to utilize the invention in various embodiments and with various modifications as are suited to the particular use contemplated.

For example, pre-acquired images obtained from different modalities may be used in place of those produced by the C-arm fluoroscope x-ray imager. Such modalities include, by way of example only, computer tomography, ultrasound, PET, or magnetic resonance imaging.

What is claimed:

1. A method for storing a trajectory of an object during a surgical procedure using a surgical navigation system, comprising:

providing at least one pre-acquired image of a patient;

tracking a three-dimensional trajectory of the object;

displaying a first representation of the object's first trajectory superimposed onto the at least one pre-acquired image;

receiving a command to store the object's first trajectory;

storing the first representation of the object's first trajectory; and superimposing a second representation of the object's second trajectory onto the at least one pre-acquired image.

2. A method for storing a trajectory of an object during a surgical procedure using a surgical navigation system, comprising:

providing at least one pre-acquired image of a patient;

tracking a three-dimensional trajectory of the object;

displaying a first representation of the object's first trajectory superimposed onto the at least one pre-acquired image;

receiving a command to store the object's first trajectory;

storing the first representation of the object's first trajectory;

superimposing a second representation of the object's second trajectory onto the at least one pre-acquired image;

receiving a plurality of commands wherein each of the plurality of commands initiates storage of the object's trajectory at a different time;

storing the object's trajectory corresponding to said different times; and superimposing a plurality of representations of the object's stored trajectories onto the at least one pre-acquired image.

3. The method of claim 2 further including:
employing directional indicators to illustrate the first representation and each of the plurality of representations, wherein each directional indicator has at least one of a different color, style, shape, size, and texture.

4. The method of claim 2 further including:
automatically assigning at least one representation with a unique label, said label being displayed adjacent to its corresponding representation.

5. The method of claim 4 wherein said label includes at least one alpha-numeric character, the character being one of generated automatically and specified manually.

6. The method of claim 2 further including:
selecting the first and second trajectory;
projecting both a tip position and hind position of the first trajectory into a plane of the at least one pre-acquired image to form a first set of projected points;
projecting both a tip position and hind position of the second trajectory into the plane of the at least one pre-acquired image to form a second set of projected points;
calculating a first segment connecting the first set of projected points;
calculating a second segment connecting the second set of projected points;
computing an angle between said first and said second segments for each pre-acquired image; and
displaying the computed angle with its respective image.

7. The method of claim 7 wherein the first and second trajectories are one of real-time trajectories and stored trajectories.

8. The method of claim 7 wherein a plurality of trajectory pairs are used to compute and display a plurality of angles.

9. A method for storing a trajectory of an object during a surgical procedure using a surgical navigation system, comprising:
providing at least one pre-acquired image of a patient;
tracking a three-dimensional trajectory of the object;
displaying a first representation of the object's first trajectory superimposed onto the at least one pre-acquired image;
receiving a command to store the object's first trajectory;
storing the first representation of the object's first trajectory;
superimposing a second representation of the object's second trajectory onto the at least one pre-acquired image;
selecting the first and second trajectory;
computing a first point based on adding a tip position of the first trajectory to an extension associated with the first trajectory;
computing a second point based on adding a tip position of the second trajectory to an extension associated with the second trajectory;
computing a distance in three-dimensional space between the first point and the second point; and
displaying the computed distance simultaneously with each image.

10. The method of claim 9 wherein the first and second trajectories are one of real-time trajectories and stored trajectories.

11. The method of claim 10 wherein a plurality of trajectory pairs are used to compute and display a plurality of distances.

12. The method of claim 1 further comprising providing a plurality of pre-acquired images taken from different orientations and simultaneously displaying more than one of the plurality of pre-acquired images.

13. The method of claim 1 wherein the pre-acquired images are images acquired by using a C-arm fluoroscope.

14. The method of claim 1 wherein the command is initiated through a software user-interface.

15. The method of claim 1 wherein the command is initiated by a foot switch.

16. An apparatus for storing a trajectory of an object during a surgical procedure using a surgical navigation system, comprising:
a computer processor;
a sensor of a three-dimensional position of the object operatively connected to the computer processor;
a memory coupled to the computer processor, storing:
at least one pre-acquired image of a patient;
instructions that when executed by the computer processor track the trajectory of the object, store the trajectory into memory upon receiving a storage command, generate representations of the tracked trajectory and the stored trajectory, and superimpose the representations onto the at least one pre-acquired image; and
a display coupled to the processor for the superimposed representations to be displayed on the at least one pre-acquired image.

17. The apparatus of claim 16 further comprising computer instructions that when executed by the computer processor:
store a plurality of tracked trajectories upon receiving additional storage commands, at least one stored trajectory representing a corresponding one of the plurality of tracked trajectories at the time the storage command is received;
generate a plurality of representations for selected ones of the plurality of stored trajectories; and
superimpose the plurality of representations of the object's stored trajectories onto the at least one pre-acquired image.

18. The apparatus of claim 17 wherein:
directional indicators are used to illustrate the tracked representation and each of the plurality of stored representations, wherein each directional indicator has at least one of a different color, style, size, shape, and texture.

19. The apparatus of claim 17 further comprising:
a plurality of unique labels that are automatically assigned by the computer processor to each stored representation, each label being displayed adjacent to its corresponding representation.

20. The apparatus of claim 19 wherein each label includes at least one alpha-numeric character, the character being one of generated automatically and specified manually.

21. The apparatus of claim 17 further comprising computer instructions that when executed by the computer processor:
select a first and second trajectory from memory;
project both a tip position and hind position of the first trajectory into a plane of at least one pre-acquired image to form a first set of projected points;
project both a tip position and hind position of the second trajectory into the plane of at least one pre-acquired image to form a second set of projected points;

calculate a first segment connecting the first set of projected points;

calculate a second segment connecting the second set of projected points;

compute the angle between said first and said second segments for each pre-acquired image; and display the computed angle simultaneously with its respective image on the display.

22. The apparatus of claim 21 wherein the first and second trajectories are one of tracked trajectories and stored trajectories.

23. The apparatus of claim 22 wherein a plurality of first and second trajectory pairs are used to compute and display a plurality of angles on the display.

24. An apparatus for storing a trajectory of an object during a surgical procedure using a surgical navigation system, comprising:

a computer processor;

a sensor of a three-dimensional position of the object operatively connected to the computer processor;

a memory coupled to the computer processor, storing:

at least one pre-acquired image of a patient;

instructions that when executed by the computer processor track the trajectory of the object, store the trajectory into memory upon receiving a storage command, generate representations of the tracked trajectory and the stored trajectory, and superimpose the representations onto the at least one pre-acquired image and further instructions that when executed by the computer processor:

select a first and second trajectory from memory;

compute a first point based on adding a tip position of the first trajectory to an extension associated with the first trajectory;

compute a second point based on adding a tip position of the second trajectory to an extension associated with the second trajectory;

compute a distance in three-dimensional space between the first point and the second point;

display the computed distance simultaneously with each image on a display; and the display coupled to the processor for the superimposed representations to be displayed on the at least one pre-acquired image.

25. The apparatus of claim 24 wherein the first and second trajectories are one of tracked trajectories and stored trajectories.

26. An apparatus for storing a trajectory of an object during a surgical procedure using a surgical navigation system, comprising:

a computer processor;

a sensor of a three-dimensional position of the object operatively connected to the computer processor;

a memory coupled to the computer processor, storing:

at least one pre-acquired image of a patient;

instructions that when executed by the computer processor track the trajectory of the object, store the trajectory into memory upon receiving a storage command, generate representations of the tracked trajectory and the stored trajectory, and superimpose the representations onto at least one pre-acquired image; and a display coupled to the processor for the superimposed representations to be displayed on the at least one pre-acquired image, wherein a plurality of first and second trajectory pairs are used to compute and display a plurality of distances between the trajectory pairs.

27. The apparatus of claim 16 further comprising a plurality of pre-acquired images taken from different orientations for simultaneous display.

28. The apparatus of claim 16 wherein the pre-acquired images are images acquired from a C-arm fluoroscope coupled to the computer processor.

29. The apparatus of claim 16 wherein the storage command is initiated through a software user-interface running on the computer processor.

30. The apparatus of claim 16 wherein the storage command is initiated by a foot switch.

31. A system for storing the trajectory of an object during a surgical procedure, comprising:

means for tracking a three-dimensional trajectory of the object;

means for providing at least one pre-acquired image of a patient to the tracking means;

means for displaying a first representation of the object's first trajectory superimposed onto the at least one pre-acquired image;

means for receiving a command to store the object's first trajectory;

means for storing the first representation of the object's first trajectory; and means for superimposing a second representation of the object's second trajectory onto the at least one pre-acquired image.

32. A system for storing the trajectory of an object during a surgical procedure, comprising:

means for tracking a three-dimensional trajectory of the object;

means for providing at least one pre-acquired image of a patient to the tracking means;

means for displaying a first representation of the object's first trajectory superimposed onto the at least one pre-acquired image;

means for receiving a command to store the object's first trajectory;

means for storing the first representation of the object's first trajectory;

means for superimposing a second representation of the object's second trajectory onto the at least one pre-acquired image;

means for receiving a plurality of commands wherein each of the plurality of commands initiates storage of the object's trajectory at a different time;

means for storing the object's trajectory at different times; and means for superimposing a plurality of representations of the object's stored trajectories onto the at least one pre-acquired image.

33. The system of claim 32 further including:

means for employing directional indicators to illustrate the first representation and each of the plurality of representations, wherein each directional indicator has at least one of a different color, style, size, shape, and texture.

34. The system of claim 32 further including:

means for automatically assigning the first representation and each of the plurality of representations with a unique label, each label being displayed adjacent to its corresponding representation.

35. The system of claim 34 wherein each label includes at least one alpha-numeric character, the character being one of generated automatically and specified manually.

36. The system of claim 32 further including:

means for selecting the first and second trajectory;

means for projecting both a tip position and hind position of the first trajectory to form a first set of projected points;

means for projecting both a tip position and hind position of the second trajectory to form a second set of projected points;

means for forming a first segment connecting the first set of projected points;

means for forming a second segment connecting the second set of projected points;

means for computing the angle between said first and said second segments for each pre-acquired image; and means for displaying the computed angle simultaneously with its respective image.

37. The system of claim 36 wherein the first and second trajectories are one of real-time trajectories and stored trajectories.

38. The system of claim 37 wherein a plurality of trajectory pairs are used to compute and display a plurality of angles.

39. A system for storing the trajectory of an object during a surgical procedure, comprising:

means for tracking a three-dimensional trajectory of the object;

means for providing at least one pre-acquired image of a patient to the tracking means;

means for displaying a first representation of the object's first trajectory superimposed onto the at least one pre-acquired image;

means for receiving a command to store the object's first trajectory;

means for storing the first representation of the object's first trajectory;

means for superimposing a second representation of the object's second trajectory onto the at least one pre-acquired image;

means for selecting the first and second trajectory;

means for computing a first point based on adding a tip position of the first trajectory to an extension associated with the first trajectory;

means for computing a second point based on adding a tip position of the second trajectory to an extension associated with the second trajectory;

means for computing a distance in three-dimensional space between the first point and the second point; and means for displaying the computed distance simultaneously with each image.

40. The system of claim 39 wherein the first and second trajectories are one of real-time trajectories and stored trajectories.

41. The system of claim 40 wherein a plurality of first and second trajectory pairs are used to compute and display a plurality of distances.

42. The system of claim 31 further comprising means for providing a plurality of pre-acquired images taken from different orientations and simultaneously displaying more than one of the plurality of pre-acquired images.

43. The system of claim 31 wherein the pre-acquired images are images acquired by using a C-arm fluoroscope.

44. The system of claim 31 wherein the command is initiated through a software user-interface.

45. The system of claim 31 wherein the command is initiated by a foot switch.

46. A method for storing paths of an object during a surgical procedure using a surgical navigation system, comprising:

providing at least one pre-acquired image of a patient;

tracking a three-dimensional path of the object;

displaying a first representation of the object's path superimposed onto the at least one pre-acquired image;

receiving at least one command to store the object's path at different times;

storing at least one object's path corresponding to said different times;

superimposing at least one representation of the object's stored path onto the at least one pre-acquired image; and computing at least one geometric measurement relating to at least one of the object's path and at least one of the stored paths.

* * * * *